(12) United States Patent
Highsmith et al.

(10) Patent No.: US 11,857,738 B2
(45) Date of Patent: Jan. 2, 2024

(54) STABILIZED CORONARY SINUS CATHETER HANDLE

(71) Applicant: Biosense Webster (Israel) Ltd., Yokneam (IL)

(72) Inventors: Debby Highsmith, Irvine, CA (US); Meir Bar-Tal, Yokneam (IL); Mohammed Pinnjara, Yokneam (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 221 days.

(21) Appl. No.: 17/111,621

(22) Filed: Dec. 4, 2020

(65) Prior Publication Data

US 2021/0178122 A1 Jun. 17, 2021

Related U.S. Application Data

(60) Provisional application No. 62/948,626, filed on Dec. 16, 2019.

(51) Int. Cl.
*A61M 25/01* (2006.01)
(52) U.S. Cl.
CPC .... *A61M 25/0136* (2013.01); *A61M 25/0138* (2013.01); *A61M 25/0147* (2013.01);
(Continued)
(58) Field of Classification Search
CPC ...... A61B 5/287; A61B 5/6855; A61B 5/6859
See application file for complete search history.

(56) References Cited

U.S. PATENT DOCUMENTS 6,302,875 B1 * 10/2001 Makower ......... A61B 17/12136
604/528
6,542,781 B1 4/2003 Koblish et al.
(Continued)

FOREIGN PATENT DOCUMENTS

EP 1383437 B1 12/2006
EP 1733689 A1 12/2006
(Continued)

OTHER PUBLICATIONS

International Search Report and Written Opinion dated May 25, 2021, from corresponding Internatinoal Application No. PCT/US2020/070906.

*Primary Examiner* — Nathan R Price
*Assistant Examiner* — Anh Bui
(74) *Attorney, Agent, or Firm* — Troutman Pepper Hamilton Sanders LLP

(57) ABSTRACT

A stabilized coronary sinus catheter system having a proximal section and a distal section with a memory shape portion, and a tip, distal of the memory shape portion. A handle having a body, a tip deflection actuator, a memory shape portion deployment actuator, and an axis. The tip is in line with the axis and the tip deflection actuator is at a first position. The tip is deflected out of alignment with the axis when the tip deflection actuator is at a second position. A third position is a delivery configuration where the memory shape portion and the tip are in line with the axis. The memory shape portion deployment actuator is at a first location. A deployed configuration allows the memory shape portion to form a predetermined shape conforming to the shape of the coronary sinus when the memory shape portion deployment actuator is at a second location.

11 Claims, 14 Drawing Sheets

(52) U.S. Cl.
CPC ............... *A61M 2025/0166* (2013.01); *A61M 2205/0266* (2013.01); *A61M 2210/125* (2013.01)

(56) References Cited

U.S. PATENT DOCUMENTS

| | | | |
|---|---|---|---|
| 6,613,046 | B1 | 9/2003 | Jenkins et al. |
| 6,745,080 | B2 | 6/2004 | Koblish |
| 6,899,711 | B2 | 5/2005 | Stewart et al. |
| 6,949,097 | B2 | 9/2005 | Stewart et al. |
| 6,972,016 | B2 | 12/2005 | Hill, III et al. |
| 7,081,115 | B2 | 7/2006 | Taimisto |
| 7,435,248 | B2 | 10/2008 | Taimisto et al. |
| 7,606,609 | B2 | 10/2009 | Muranushi et al. |
| 7,917,187 | B2 | 3/2011 | Fuimaono et al. |
| 7,959,630 | B2 | 6/2011 | Taimisto et al. |
| 8,257,351 | B2 | 9/2012 | Stewart et al. |
| 8,620,400 | B2 | 12/2013 | de la Rama et al. |
| 8,834,464 | B2 | 9/2014 | Stewart et al. |
| 8,945,110 | B2 | 2/2015 | Fish et al. |
| 9,554,848 | B2 | 1/2017 | Stewart et al. |
| 9,585,587 | B2 | 3/2017 | Roy et al. |
| 9,717,555 | B2 | 8/2017 | Chan et al. |
| 9,788,893 | B2 | 10/2017 | Ditter |
| 9,795,315 | B2 | 10/2017 | Bullinga |
| 9,918,791 | B2 | 3/2018 | Bui et al. |
| 10,130,422 | B2 | 11/2018 | Ditter |
| 2001/0007070 | A1 | 7/2001 | Stewart et al. |
| 2002/0004631 | A1 | 1/2002 | Jenkins et al. |
| 2002/0049485 | A1* | 4/2002 | Smits .................... A61N 1/056 607/122 |
| 2002/0165536 | A1* | 11/2002 | Kelley .................... A61N 1/05 606/41 |
| 2003/0153967 | A1 | 8/2003 | Koblish et al. |
| 2003/0195406 | A1 | 10/2003 | Jenkins et al. |
| 2005/0010095 | A1 | 1/2005 | Stewart et al. |
| 2005/0015084 | A1 | 1/2005 | Hill, III et al. |
| 2005/0234436 | A1* | 10/2005 | Baxter ............... A61B 18/1492 606/41 |
| 2006/0106298 | A1* | 5/2006 | Ahmed ............... A61B 18/1492 606/41 |
| 2006/0200171 | A1 | 9/2006 | Teague |
| 2010/0069733 | A1 | 3/2010 | Kastelein et al. |
| 2010/0198041 | A1 | 8/2010 | Christian et al. |
| 2014/0257138 | A1 | 9/2014 | Hui et al. |
| 2015/0208937 | A1 | 7/2015 | Bullinga |
| 2016/0242662 | A1 | 8/2016 | Gibson et al. |
| 2016/0331325 | A1 | 11/2016 | Munsinger et al. |
| 2017/0065226 | A1 | 3/2017 | Osypka et al. |
| 2019/0015628 | A1 | 1/2019 | Kawaguchi |
| 2019/0046062 | A1* | 2/2019 | Yankelson ............. A61N 1/056 |

FOREIGN PATENT DOCUMENTS

| | | |
|---|---|---|
| EP | 2208474 A2 | 7/2010 |
| EP | 2263588 A2 | 12/2010 |
| EP | 2664295 A1 | 11/2013 |
| EP | 2712567 A1 | 4/2014 |
| EP | 1233716 B1 | 7/2014 |
| EP | 2803329 A1 | 11/2014 |
| EP | 3023069 A1 | 5/2016 |
| EP | 1663044 B1 | 2/2017 |
| WO | 01037723 A2 | 5/2001 |
| WO | 02045608 A2 | 6/2002 |
| WO | 02083017 A1 | 10/2002 |
| WO | 02087453 A1 | 11/2002 |
| WO | 2004100813 A2 | 11/2004 |
| WO | 2005030072 A1 | 4/2005 |
| WO | 2006096359 A1 | 9/2006 |
| WO | 2017159007 A1 | 9/2017 |
| WO | 2017199240 A2 | 11/2017 |
| WO | 2018085062 A1 | 5/2018 |

\* cited by examiner

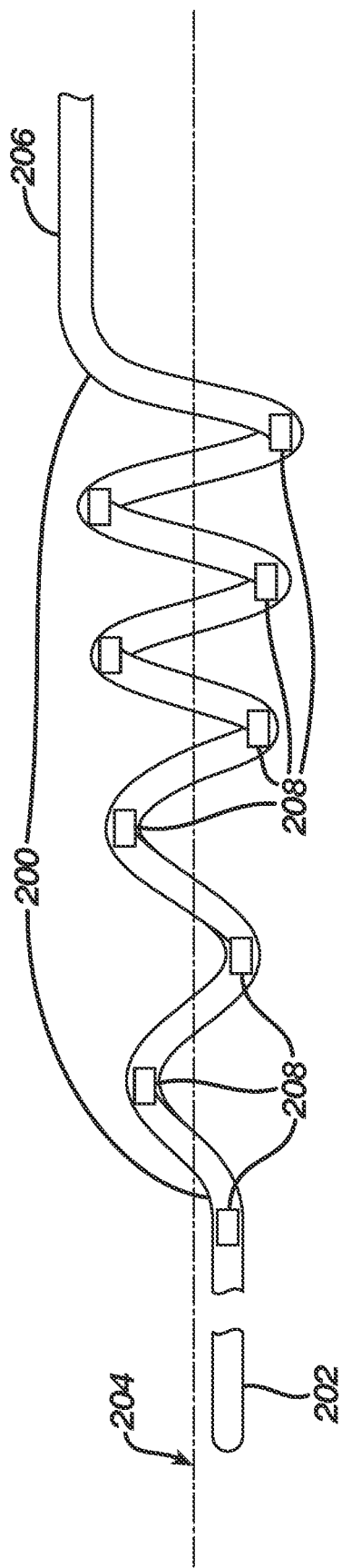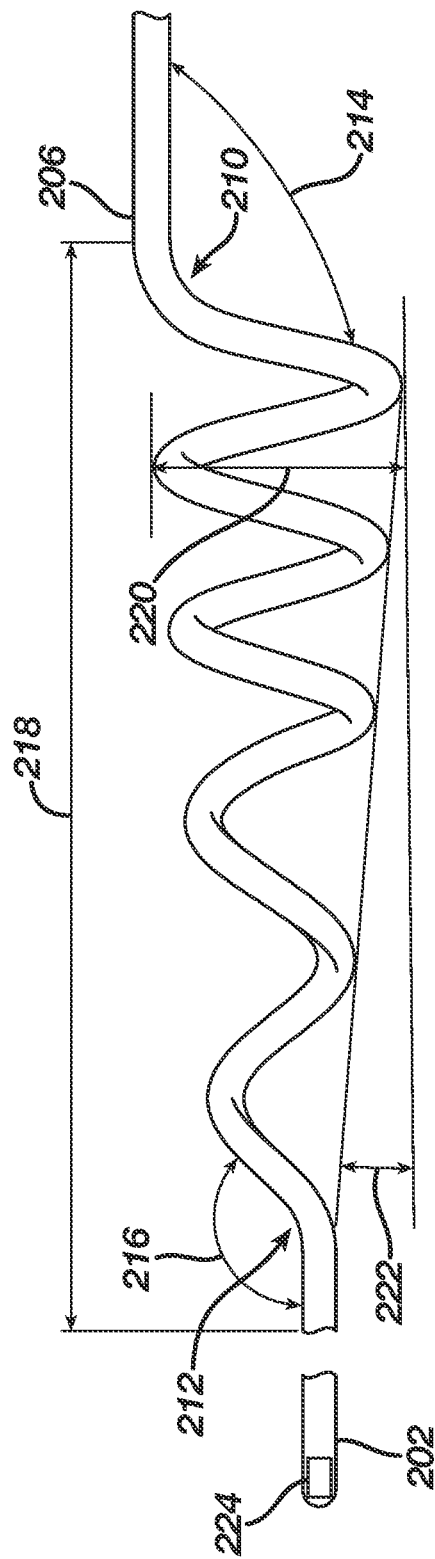

STABILIZED CORONARY SINUS CATHETER HANDLE

CROSS REFERENCE TO RELATED APPLICATION

This application claims the benefit of priority under 35 U.S.C. §§ 119 and 120 to prior filed U.S. Provisional Patent Application No. 62/948,626 filed on Dec. 16, 2019 which is hereby incorporated by reference as set forth in full herein.

FIELD

The present disclosure generally relates to a control handle for CS catheter systems, and more particularly, the present disclosure to relates to improved handles for steerable catheters which can be operated with one hand.

BACKGROUND

During an electrophysiological (EP) cardiac procedure, a coronary sinus (CS) catheter may be inserted into the heart, to provide a reference for the procedure. The CS catheter has electrodes on its surface, and the signals acquired by the electrodes are used as references for other signals acquired in the procedure, such as for EP mapping of heart chambers. In order to act as a good reference, the CS catheter should not move within its retaining chamber (the CS), or any movement must be allowed for.

While methods for allowing for movement are known in the art, it is preferable that the CS remain catheter is fixed in position. Additionally, while it is known to deploy a CS catheter with shape memory properties to stabilize the catheter in the CS, the prior art can place too much stress both on the catheter and the inferior vena cava leading to the right atrium. In addition, guiding the catheter to the coronary sinus can also be cumbersome.

Existing catheters, even those with steerability and deflection control, often have limited maneuverability capabilities. This is especially true of procedures where particularly fine movement control is required. Further, existing designs can require two hands or be difficult to control. A physician needing to repeatedly look away from his diagnostic tools to see where his hand is located and what part of the handle needs to be actuated can add considerable time to an operation procedure.

Further, electrode catheters are used to stimulate and map electrical activity in the heart and to ablate sites of aberrant electrical activity. In use, the electrode catheter is inserted into a major vein or artery, e.g., femoral artery, and then guided into the chamber of the heart which is of concern. Within the heart, the ability to control the exact position and orientation of the catheter tip is critical. Any instability with an electrode catheter can therefore affect results of a related procedure (e.g., unreliable results of cardiac mapping) and thus be significant to the success of a particular procedure.

There is therefore a need for improved devices, systems, and methods for control handles capable of fine steering control of a catheter while also able to actuate further functions, such as the expansion of the sensor anchoring coil. It is also highly preferable that the articulation of these functions can be performed with a single hand, such that the ergonomics of the handle do not impart fatigue on the operator.

SUMMARY

To that end, the present disclosure is a stabilized coronary sinus catheter system having a proximal section and a distal section with a memory shape portion, and a distal tip, distal of the memory shape portion. A handle can be disposed proximal of the proximal section having a body, a distal tip deflection actuator, a memory shape portion deployment actuator, and a center axis. The distal tip deflection actuator has a first position where the distal tip is approximately in line with the center axis. It also has a deflected state when the distal tip deflection actuator is at a second position and the distal tip is deflecting out of alignment with the center axis. A third position of the distal tip deflection actuator can have the memory shape portion and the distal tip approximately in line with a center axis and the memory shape portion deployment actuator at a first location. Further, the memory shape portion can be deployed, forming a predetermined shape approximately conforming to the shape of the coronary sinus when the memory shape portion deployment actuator is at a second location.

The stabilized coronary sinus catheter system can further have a pull wire with a first end anchored in the distal tip, and a second end fixed in the body. The distal tip deflection actuator can be attached to the pull wire, and the second position displaces the pull wire. The distal tip has a deflection angle between approximately 0° and approximately 180°.

The coronary sinus catheter further has a medial section, distal of the proximal section, having a medial stiffness, the proximal section includes a proximal stiffness, and the distal tip has a flexibility greater than the proximal stiffness, the medial stiffness, and a stiffness of the shape memory portion. A single axis location sensor can be disposed approximately at the distal tip.

Further, the system has a deflection actuator lock having an unlocked position permitting the distal tip deflection actuator to move between the first position and the second position, and a locked position preventing the distal tip deflection actuator to move between the first position and the second position.

A shape memory alloy can be disposed along the shape memory portion and having one end fixed in the body. A cover tube can be disposed over a portion of the shape memory alloy and having a memory shape portion deployment end fixed to the memory shape portion deployment actuator. In the delivery configuration the cover tube constrains the shape memory alloy, and in the deployed configuration the shape memory alloy is unconstrained by the cover tube.

When the memory shape portion deployment actuator is at the first location, it maintains the cover tube over the shape memory alloy which prevents the shape memory alloy from returning to the predetermined shape. When the memory shape portion deployment actuator is at the second location, it withdraws the cover tube away from the shape memory alloy allowing the shape memory alloy to return to the predetermined shape.

In one example, the stabilized coronary sinus catheter system's predetermined shape of the shape memory portion is approximately a helical shape. The predetermined shape of the shape memory portion has at least one of:
   a proximal section bending radius between approximately 8.5 mm and approximately 9.5 mm,
   a distal section bending radius between approximately 7.0 mm and approximately 8.0 mm,
   a proximal section helix angle between approximately 110° and approximately 120°,
   a distal section helix angle between approximately 150° and approximately 160°, a shape memory portion length between approximately 42.5 mm and approximately 44.5 mm, a major diameter of a first helix coil approximately 14.0 mm and approximately 16.0 mm, and/or a taper angle between approximately 3.5° and approximately 5.5°.

A method of using a coronary sinus catheter to map electrical activity of a heart, the coronary sinus catheter having a distal section having a memory shape portion, and a distal tip, distal of the memory shape portion. A handle is also included disposed proximal of the proximal section having a body, a distal tip deflection actuator, a memory shape portion deployment actuator, a cover tube disposed over a portion of the memory shape portion, and a center axis. The method includes the steps of delivering the coronary sinus catheter to the coronary sinus in a delivery configuration so that a distal section of the coronary sinus catheter is approximately in line with a center axis. Then deflecting the distal tip out of alignment with the center axis to steer the coronary sinus catheter by actuating the distal tip deflection actuator. And, then, deploying the memory shape portion of the distal section of the coronary sinus catheter in the coronary sinus, having the steps of withdrawing the cover tube from the memory shape portion, and returning the memory shape portion to a preformed shape. Once deployed, there is a step of applying a lateral force against the coronary sinus with the memory shape portion.

A different example of a stabilized coronary sinus catheter can have a main sensor probe having a plurality of main sensors disposed along a first length of the main sensor probe. Also, a plurality of secondary sensor probes each having a second length shorter than the first length, and a secondary sensor disposed on the distal position. There can be a sheath catheter having a lumen configured to allow the main sensor probe and the plurality of secondary sensor probes to pass therethrough. In a sheathed position, the plurality of secondary sensor probes are enclosed in the lumen, and at least a portion of the main sensor probe is outside the lumen. In an unsheathed position, both the main sensor probe and the plurality of secondary sensor probes are outside the lumen, and the plurality of secondary sensor probes angle away from the main sensor probe and apply a lateral force against the coronary sinus.

The second length has a plurality of sub lengths, and a portion of the plurality of secondary sensor probes each have a different sub length. Further included is a midline axis and the main sensor probe is disposed approximately along the midline axis. The plurality of secondary sensor probes are approximately parallel to the midline axis in the sheathed position and form an angle away from the midline axis in the unsheathed position.

A secondary sensor probe angle can be formed between a secondary sensor probe and the midline axis with an angle between approximately 0° and approximately 90° and, more preferred, the secondary sensor probe angle can be between approximately 0° and approximately 10°.

BRIEF DESCRIPTION OF THE DRAWINGS

FIGS. 2A and 2B are side views of an example of a distal section of the stabilized coronary sinus catheter of the present disclosure.

DETAILED DESCRIPTION

Figure 1:
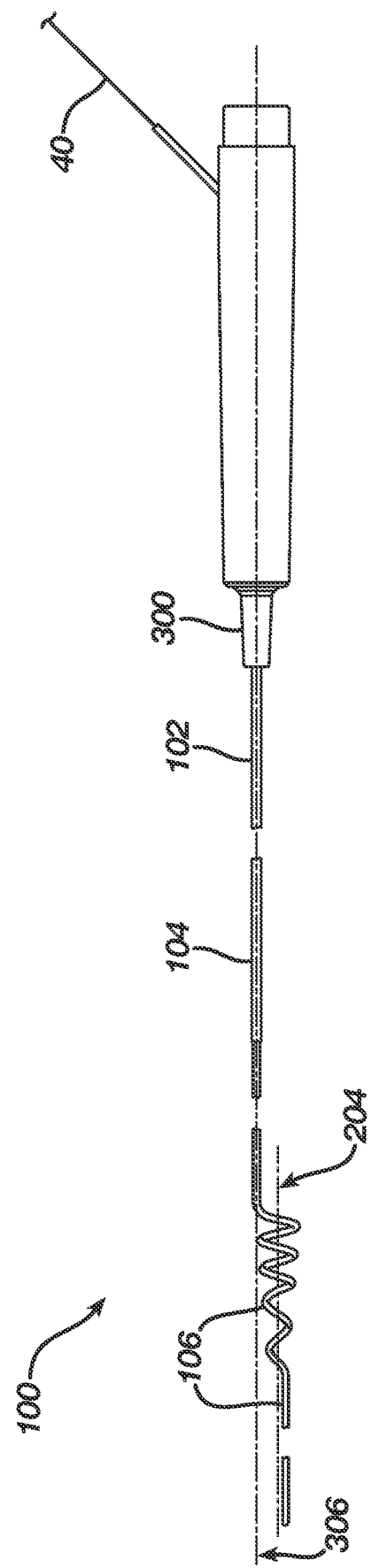
FIG. 1 is a side view of an example of a stabilized coronary sinus catheter of the present disclosure.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%.

As used herein, a "subject" or "patient", including a blood vessel from a subject or a patient, may refer to any applicable human patient as well as any mammal, veterinarian animal, livestock animal or pet type animal, etc. As an example, the animal may be a laboratory animal specifically selected to have certain characteristics similar to a human (e.g., rat, dog, pig, rabbit, monkey, or the like).

As used herein, "operator" may include a doctor, surgeon, or any other individual or instrumentation associated with the medical procedure used with the device(s) of this disclosure.

In addition, the terms "patient," "host," "user," and "subject" refer to any human or animal subject and are not intended to limit the systems or methods to human use, although use of the subject disclosure in a human patient represents a preferred embodiment.

As used herein, the term "computing system" is intended to include stand-alone machines or devices and/or a combination of machines, components, modules, systems, servers, processors, memory, detectors, user interfaces, computing device interfaces, network interfaces, hardware elements, software elements, firmware elements, and other computer-related units. By way of example, but not limitation, a computing system can include one or more of a general-purpose computer, a special-purpose computer, a processor, a portable electronic device, a portable electronic medical instrument, a stationary or semi-stationary electronic medical instrument, or other electronic data processing apparatus.

As used herein, the terms "component," "module," "system," "server," "processor," "memory," and the like are intended to include one or more computer-related units, such as but not limited to hardware, firmware, a combination of hardware and software, software, or software in execution. For example, a component may be, but is not limited to being, a process running on a processor, an object, an executable, a thread of execution, a program, and/or a computer. By way of illustration, both an application running on a computing device and the computing device can be a component. One or more components can reside within a process and/or thread of execution and a component may be localized on one computer and/or distributed between two or more computers. In addition, these components can execute from various computer readable media having various data structures stored thereon.

The components may communicate by way of local and/or remote processes such as in accordance with a signal having one or more data packets, such as data from one component interacting with another component in a local system, distributed system, and/or across a network such as the Internet with other systems by way of the signal. Computer readable medium can be non-transitory. Non-transitory computer-readable media include, but are not limited to, random access memory (RAM), read-only memory (ROM), electronically erasable programmable ROM (EEPROM), flash memory or other memory technology, compact disc ROM (CD-ROM), digital versatile disks (DVD) or other optical storage, magnetic cassettes, magnetic tape, magnetic disk storage or other magnetic storage devices, or any other tangible, physical medium which can be used to store computer readable instructions and/or data.

As used herein, the term "trace" includes a conductive path in an electrical circuit such as a path integral to a printed circuit, an individual wire, a conductor within a ribbon cable, or other such structure as appreciated and understood by a person of ordinary skill in the art according to the teachings of the present disclosure.

As used herein, the terms "tubular" and "tube" are not limited to a structure that is a right cylinder or strictly circumferential in cross-section or of a uniform cross-section throughout its length. For example, the tubular structure or system is generally illustrated as a substantially right cylindrical structure. However, the tubular system may have a tapered outer surface, a curved outer surface, and/or a partially flat outer surface without departing from the scope of the present disclosure.

Figure 5:
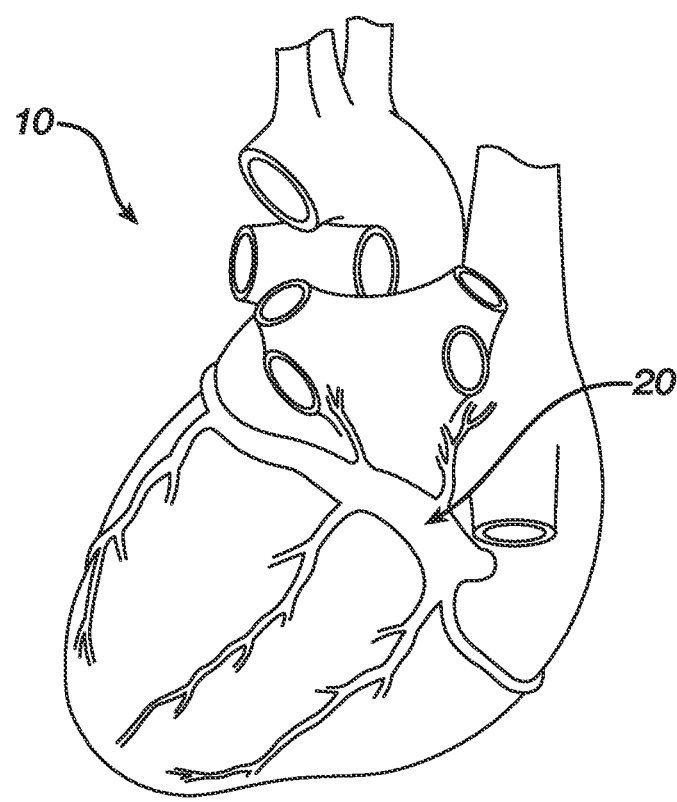
FIG. 5 is an image of a heart identifying the coronary sinus.
Figure 6:
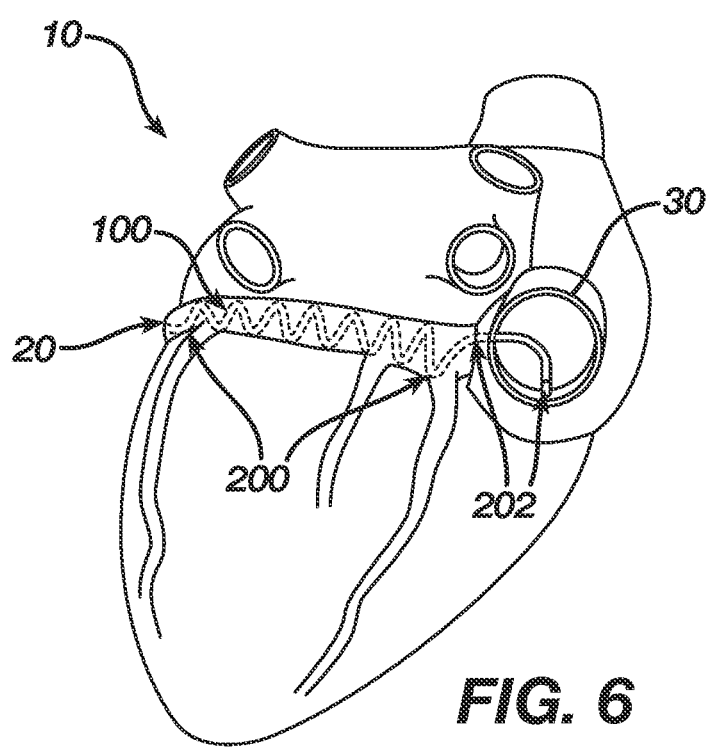
FIG. 6 is an image of an example of a stabilized coronary sinus catheter of the present disclosure fully deployed in the coronary sinus.

Turning now to FIG. 1, it illustrates a stabilized coronary sinus catheter system that includes a coronary sinus catheter 100 configured to enter the coronary sinus 20 of a heart 10 (see FIGS. 5 and 6). During an electrophysiological (EP) cardiac procedure, the coronary sinus (CS) catheter 100 may be inserted into the heart 10, to provide a reference for the procedure. The CS catheter 100 has a proximal section 102, a medial section 104 and a distal section 106. A handle 300 can be disposed proximal of the proximal section 102 to allow the use to control the movement and deployment of the features of the CS catheter 100. The medial section 104 can be distal of the proximal section 102 and have a medial stiffness. The proximal section 102 can have a proximal stiffness and the distal tip 202 can have a flexibility greater than the proximal stiffness, the medial stiffness, and a stiffness of the shape memory portion 200.

While stiffness is a general term, there are many ways to form the catheter sections 102, 104, 106 with different stiffness or conversely, flexibility. Each section can be formed from one or more polymers and or materials having different hardness or durometer. Additionally, braids or other stiffeners can be used inside, around the outside or molded directly into the catheter sections 102, 104, 106. Alternately or additionally, strain relief features (such as physical scoring) can be added to increase flexibility.

FIGS. 2A and 2B illustrate the features of the distal section 106. The distal section 106 can have electrodes or sensors 208 along its surface. The signals acquired by the sensors 208 are used as references for other signals acquired in the procedure, such as for EP mapping of heart 10. In order to act as a good reference, the CS catheter 100 should not move within its retaining chamber (the CS 20), or any movement must be allowed for. To that end, the distal section 106 also includes a memory shape portion 200 and a distal tip 202, distal of the memory shape portion 200. FIGS. 2A and 2B illustrate the memory shape portion 200 in a deployed configuration. Here, the memory shape portion 200 forms a predetermined shape approximately conforming to the shape of the coronary sinus 20. Shapes can include a helix or basket. When the memory shape portion 200 takes the deployed shape (and in this example, a helical shape), the electrodes 208 are pushed into contact with the CS 20 wall. The pressure of the memory shape portion 200 into the wall locks the catheter 100 in position. The distal tip 202 can also include a single axis location sensor 224 to help guide it into the CS 20 before the sensors 208 are deployed.

Figure 3:
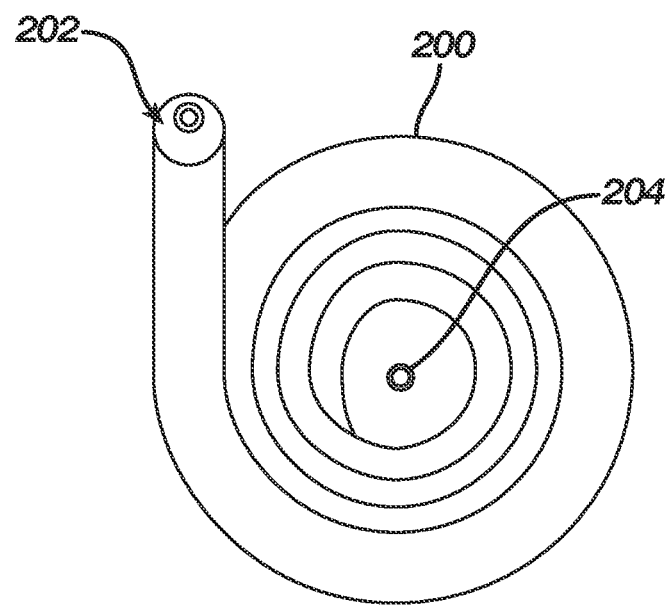
FIG. 3 is a front view of an example of a distal section of the stabilized coronary sinus catheter of the present disclosure.

To facilitate the locking aspect, the memory shape portion 200 has a proximal end 206 and a distal section axis 204 running from the proximal end 206 to the distal tip 202. In the example illustrated in FIGS. 2A, 2B and 3, the predetermined shape of the shape memory portion 200 has some exemplary measurements when in a tapered helical shape. A proximal section bending radius 210 can measure between approximately 8.5 mm and approximately 9.5 mm and a distal section bending radius 212 can be between approximately 7.0 mm and approximately 8.0 mm. A proximal section helix angle 214 can be between approximately 110° to approximately 120°. A distal section helix angle 216 can be between approximately 150° to approximately 160°. The shape memory portion can have a length 218, when deployed between approximately 42.5 mm to approximately 44.5 mm. A major diameter 220 of a first helix coil can be approximately 14.0 mm to approximately 16.0 mm, and a taper angle 222 between approximately 3.5° and approximately 5.5°.

Figure 4:
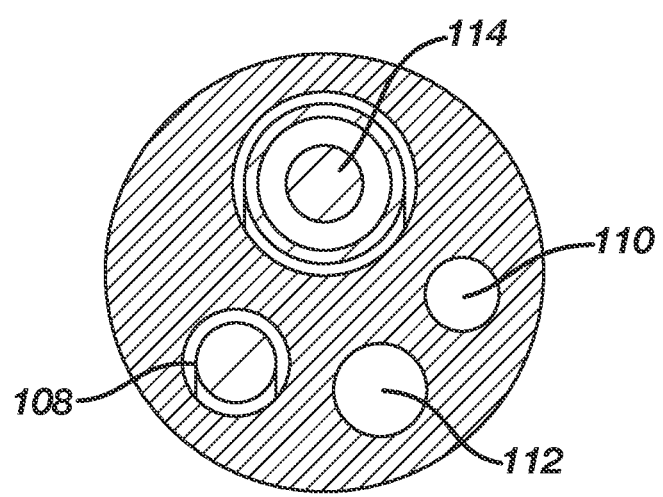
FIG. 4 is a cross-sectional view of the distal end of the stabilized coronary sinus catheter of FIG. 3.
Figure 14:
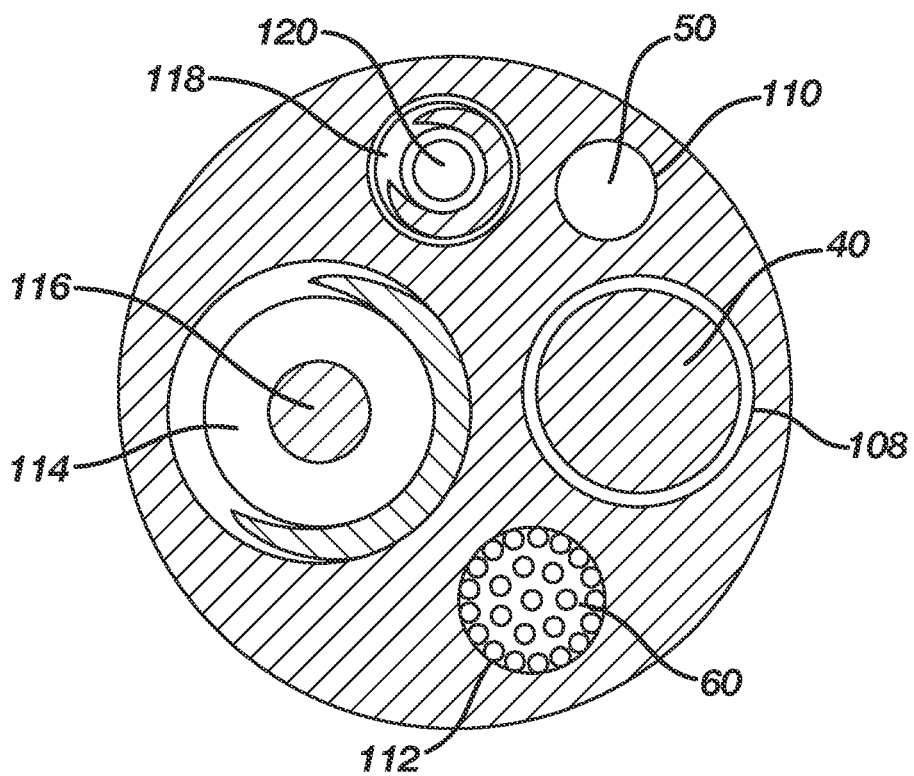
FIG. 14 is a cross-section of a stabilized coronary sinus catheter having additional lumens.

FIG. 4 illustrates an example of a cross-section of the catheter 100. In this example, there can be a guide wire lumen 108 that allows the catheter 100 to ride over a guide wire 40 to guide the catheter 100 from the insertion point (typically a groin puncture) to the heart 10. Once near or in the CS 20, the guide wire 40 can be removed to allow for the further functionality of the handle 300, which is described in more detail below. A sensor wire lumen 110 can contain a sensor wire 50 (see FIG. 14) connecting the sensors 208 back to a system to read the data from the sensors and display it for the user. In one example, there can be at least forty (40) sensors 208 deployed along the distal section 106. The sensor wire 50 can also transmit signals from the single axis location sensor 224. The movement of the catheter 100 is tracked with at least the single axis location sensor 224 to allow for proper placement in the CS 20. Once the catheter 100 is properly placed and the shape memory portion 200 is deployed, the catheter 100 is tracked and the CS chamber is fully demonstrated in a mapping system for a user. Tracking of the catheter 100 can use any known tracking technology such as CARTO®.

In the example of the shape memory portion 200 illustrated in FIGS. 5 and 6, its helical structure also serves as anchoring mechanism that locks the catheter 100 in place in the CS 20. This also places the sensors 208 in continuous contact in the CS 20 chamber walls to provide a stable reading free from the artifacts like heart beat and respiration. These are improvements over prior art CS catheters. Electrocardiogram (ECG) artifacts are generated from the inter-motion between the electrodes and the CS wall during the heart retraction and movements related to the respiratory related motion.

As the shape memory portion 200 anchors the catheter 100, the distal tip 202 following medial section 104 is used as strain relief. Being radially soft, the retraction of the guide-wire can leave this section handing in the right atria with minimal applied force on the shape memory portion 200. As the proximal section 102 can be firmer, pushing it somewhat forward after the guide-wire is fully retracted, builds in a section of strain relief. This prevents motion of the heart due to respiration and heartbeat from applying forces in the shape memory portion 200. This can further prevent risk of movement of the shape memory portion 200 in the CS 20. With the catheter 100 firmly stable in the CS 20, any motion of the catheter 100 is monitored and used to alert the mapping system and user.

Having many sensors 208 (with an example of 2-3 mm spacing) surrounding the CS 20 chamber, allows selection of the sensors 208 that have atria activity or ventricle activity to permit selective detection of atria or ventricle activity. Moreover, in the case of left and right atria disassociation, each atria activity can be tracked independently. The sensors 208 can be oriented to be sensitive both along and transverse to the distal section axis 204, providing an accurate view of activity in any direction. This can be achieved by taking a wide bipolar signal for subtracting not just the nearest neighbor electrode. Having a full view of the CS 20 provides better tracing of the activation morphology, which represents both the FAR field (activity further from the CS 20) and the near field (activity related to ECG originated near the CS 20). This capability provides a more robust tracking tool allowing detection of similar ECG activities and support stitching different positions of a mapping catheter (as is used by CARTO® during LAT mapping). Some of the tachycardia involves activation in the CS 20. Mapping the CS 20 is challenging with current tools as the activity may be on the side proximal to the heat wall or opposite. With the shape memory portion 200 in a helical shape, a full activation map in the CS is possible.

Other elements of the catheter 100 are the lead wire lumen 112 and the shape memory lumen 114. The shape memory lumen 114 contains a shape memory alloy 116 (see FIG. 14). The shape memory alloy 116 can be made from a material capable of recovering its shape automatically once released from a highly strained delivery configuration. A superelastic shape memory material such as Nitinol or an alloy with similar properties is particularly suitable. These materials have sufficient elastic strain capacity such that the elastic limit would not be exceeded when the shape memory portion 200 is constrained in a delivery configuration. This elastic strain capacity allows the shape memory portion 200 to self-expand when deployed. The shape memory lumen 114 can run the length of the catheter 100, or in one example is only the length of the shape memory portion 200 or distal section 106.

The catheter 100 can also include a pull wire lumen 118 containing a pull wire 120. The pull wire 120 can be used to deflect the distal tip 202. The pull wire 120 can be anchored at its proximal end to the handle (described in more detail below). The pull wire 120 can be made of any suitable metal, such as stainless steel or Nitinol, and is preferably coated with Teflon7 or any other coating that imparts lubricity to the pull wire 120.

Figure 7A:
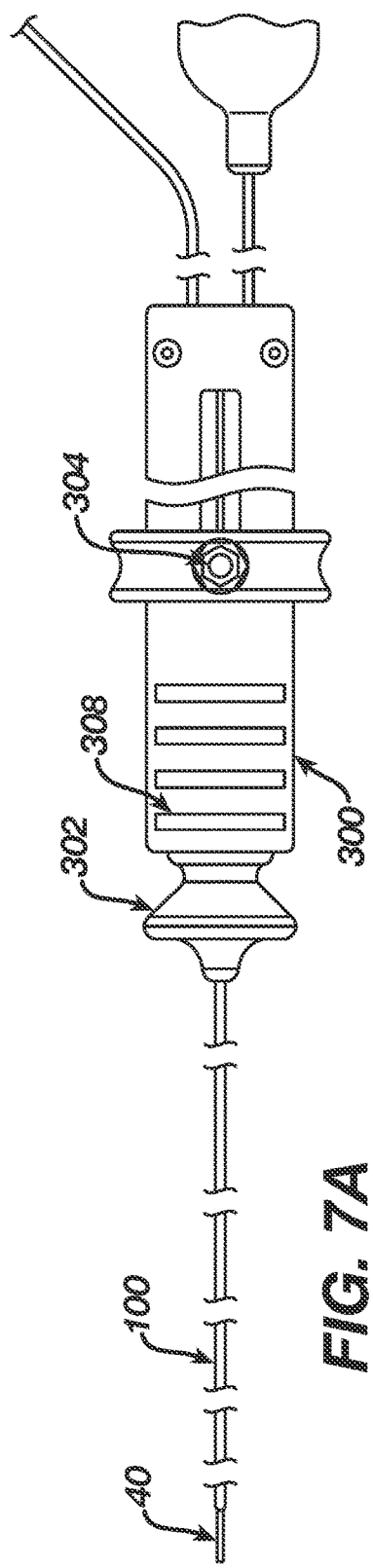
FIGS. 7A-7C illustrate and example of a handle with a deflection tip and a sequential deployment of the helical section.

FIGS. 7A-13 illustrate different examples of the handle 300. The handle 300 can include a body 301, a distal tip deflection actuator 302, a memory shape portion deployment actuator 304, and a center axis 306. The handle 300 is designed for ease of use. FIG. 7A illustrates the handle controls 302, 304 in a neutral position and delivery configuration. In the neutral position the distal tip 202 can be approximately in line with the center axis 306. In the neutral position the distal tip deflection actuator 302 is at a first position. The first position is the most proximal position of the distal tip deflection actuator 302. FIG. 7A also illustrates the delivery configuration where the memory shape portion 200 and the distal tip 202 are approximately in line with a center axis 306. Here, the memory shape portion deployment actuator 304 can be at its most distal position. The distal tip deflection actuator 302 is at the first position and the memory shape portion deployment actuator 304 is at its first location. The neutral position and delivery configuration allow the catheter 100 to ride over the guidewire 40 to deliver the distal section 106 into the CS 20.

Figure 7B:
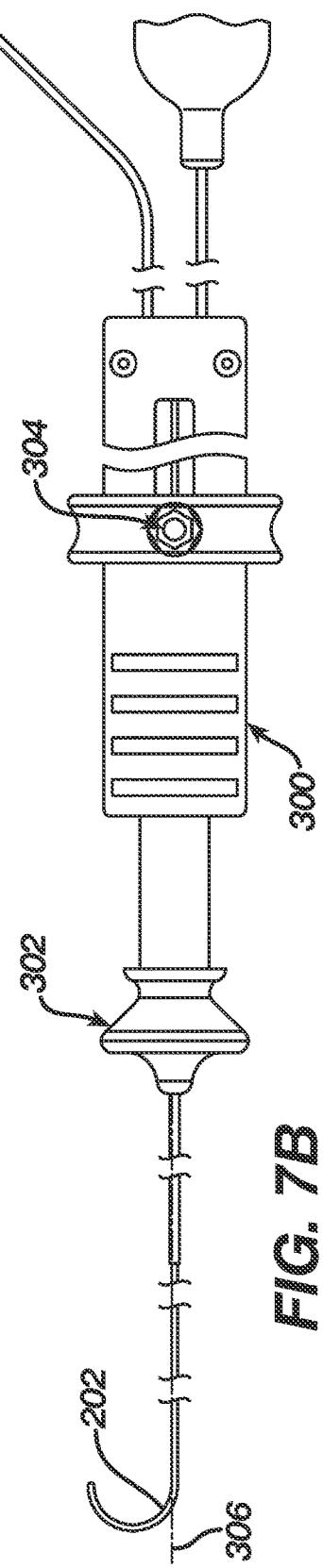
Figure 7C:
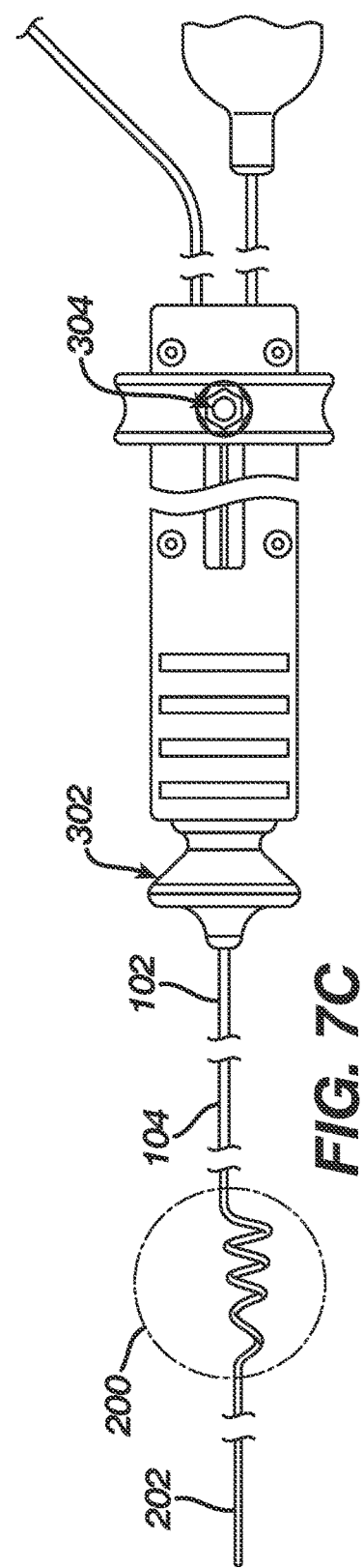
Figure 8:
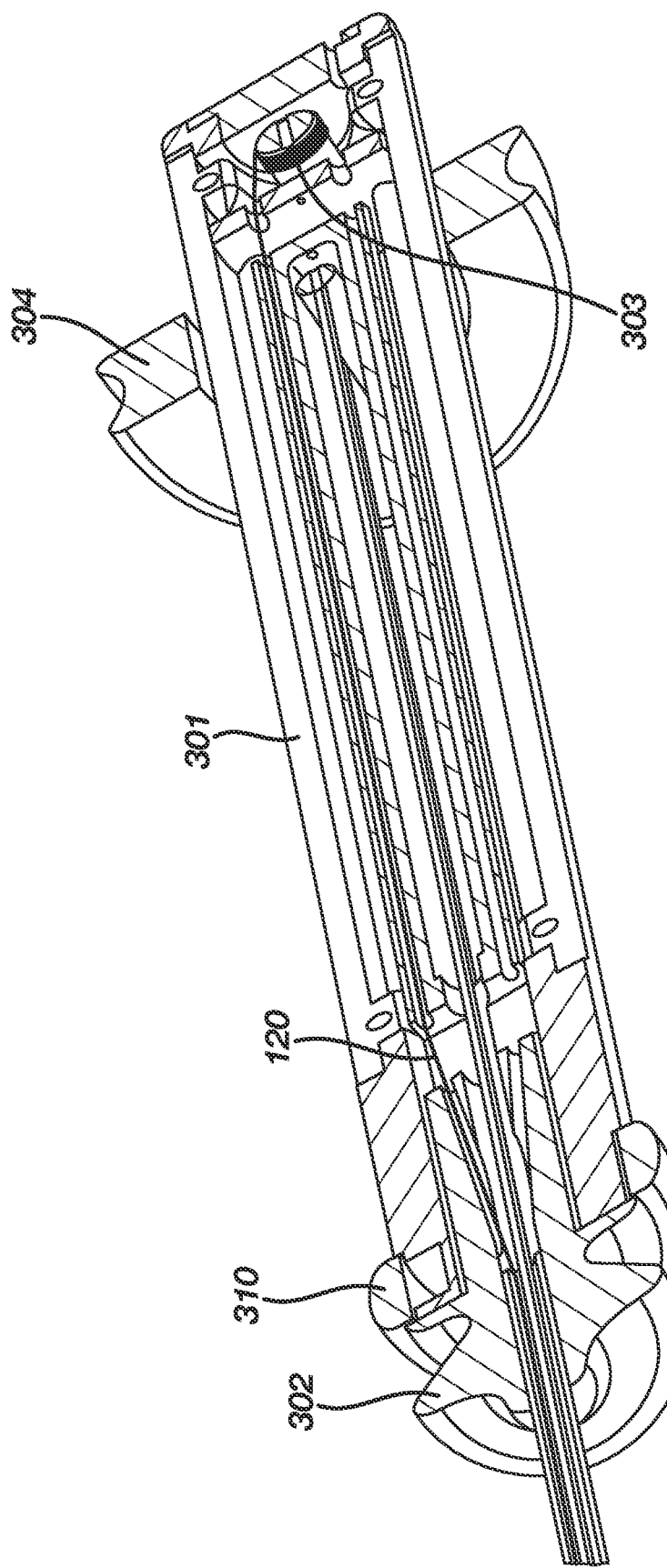
FIG. 8 is a cross-section of an example of a handle of the present disclosure illustrating the elements involved in tip deflection.

FIG. 7B illustrates the handle 300 and catheter 100 in a deflected position. Here, the guidewire 40 has been removed, either completely or into the medial section 104 and the distal tip 202 is deflecting out of alignment with the center axis 306. The deflection can be caused by the distal tip deflection actuator 302 being moved to a second position, more distal than the first. FIGS. 8, 9A, 9B, and 13 illustrate the deflection mechanism. The pull wire 120 has a first end anchored in the distal tip 202 and a second end attached to a fixed point 303 (a tension screw as illustrated) in the body 301. The distal tip deflection actuator 302 can be attached to the pull wire 120 such that any movement along the center axis 306 displaces the pull wire 120. Extending the distal tip deflection actuator 302 can cause the distal tip 302 to deflect over a deflection angle between approximately 0° and approximately 180°. Deflecting the distal tip 202 allows the distal section 106 to be directed to the proper position within the CS 20 and the distal tip 202 in to the inferior vena cava (FIG. 6).

Figure 9A:
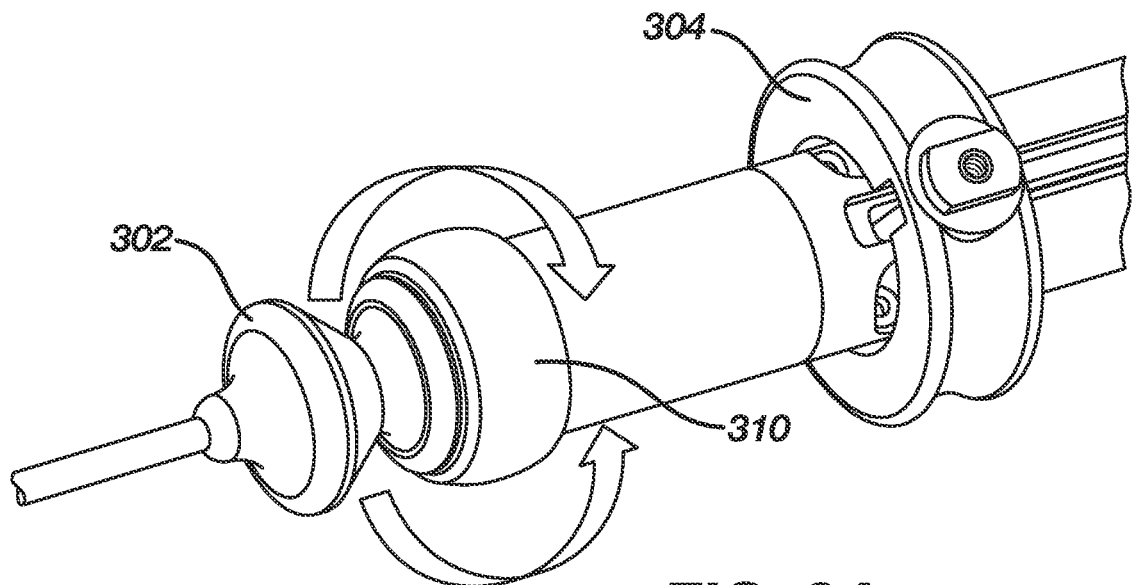
FIGS. 9A and 9B illustrate a piston movement of the handle to deflect the tip of the catheter.
Figure 9B:
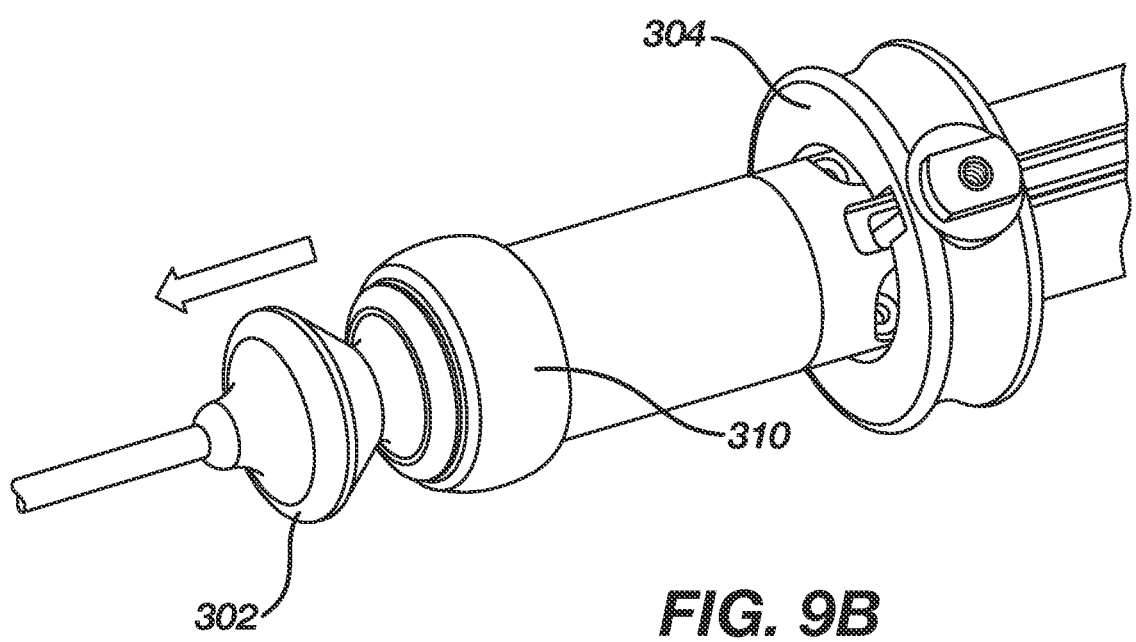

FIGS. 9A and 9B illustrate the locked and unlocked position of a deflection actuator lock 310. In this example, a simple twist can lock and unlock the ability to deflect the distal tip 202. Thus, the deflection actuator lock 310 has an unlocked position permitting the distal tip deflection actuator 302 to move between the first position (most proximal) and the second position (most distal). Also, the locked position prevents the distal tip deflection actuator 310 from moving between the first position and the second position. Additionally, a handle deflection brake 308 is apparent on the handle 300 to have stops at different deflection angles so the user can look at the handle 300 and determine how much the distal tip 202 is deflected. The distal tip 202 can be deflected when the shape memory portion 200 is undeployed and/or in the delivery configuration.

FIGS. 7C and 10-13 illustrate the deployed configuration of the shape memory portion 200. The shape memory alloy 116, as noted above, can be disposed at least along the shape memory portion 200 and comprising one end fixed in the body 301. The shape memory alloy 116 has been preset to an expanded shape that is configured to anchor the distal section 106 of the coronary sinus catheter 100 in the coronary sinus 20. As illustrated, that preset shape is a helix offset from the center axis 306, but any shape can be considered that is atraumatic and can fit to the walls of the CS 20.

To facilitate the delivery and deployed configurations, a cover tube 312 can be disposed over the shape memory portion 200 or even a portion of the shape memory alloy 116. In one example, the cover tube 312 can have a memory shape portion deployment end 314 fixed to the memory shape portion deployment actuator 304. In the delivery configuration, the cover tube 312 constrains the shape memory portion 200/shape memory alloy 116 and in the deployed configuration the shape memory portion 200/shape memory alloy 116 is unconstrained by the cover tube 312.

Figure 10:
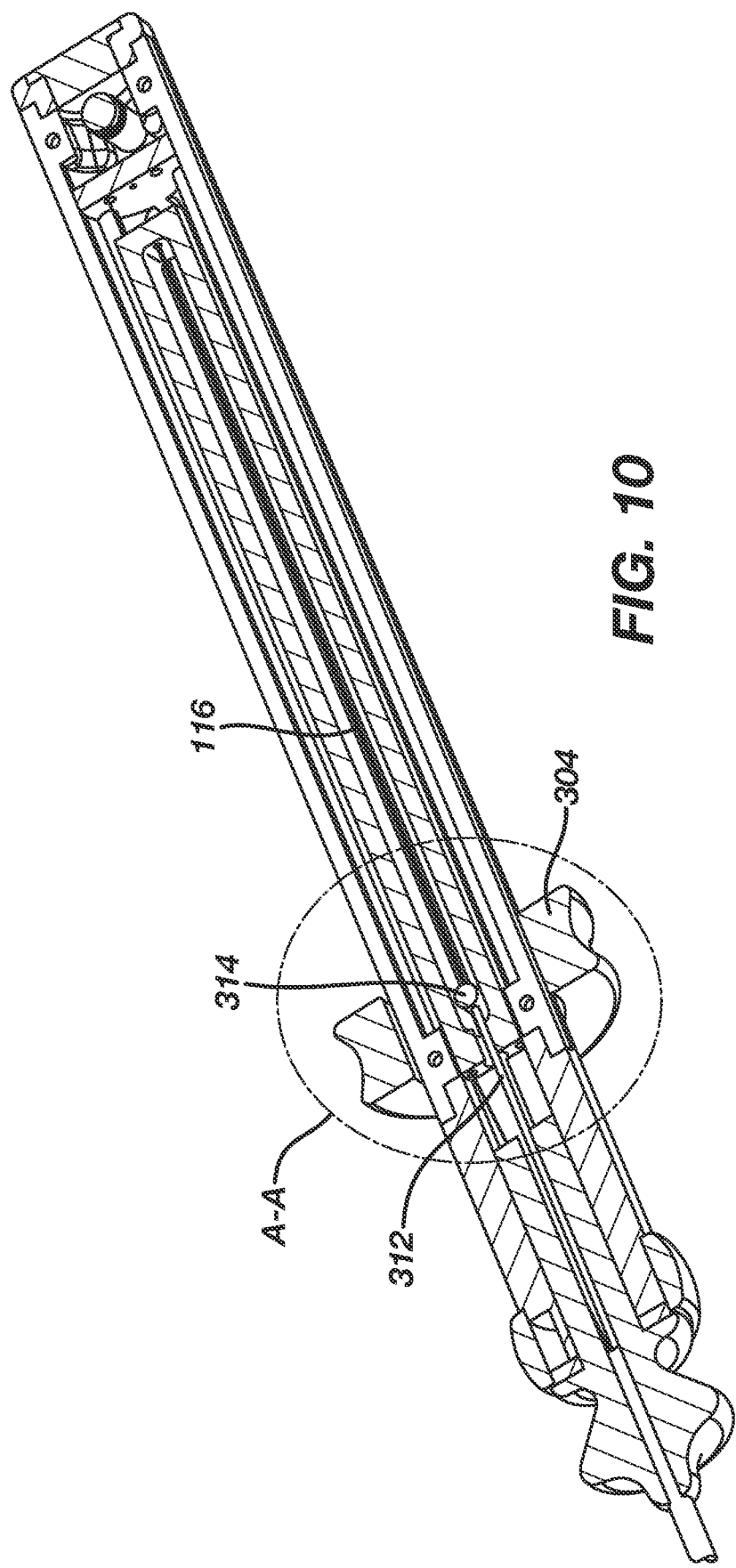
FIG. 10 is a cross-section of an example of a handle of the present disclosure illustrating the elements involved in deploying the helical section in the undeployed position.
Figure 11:
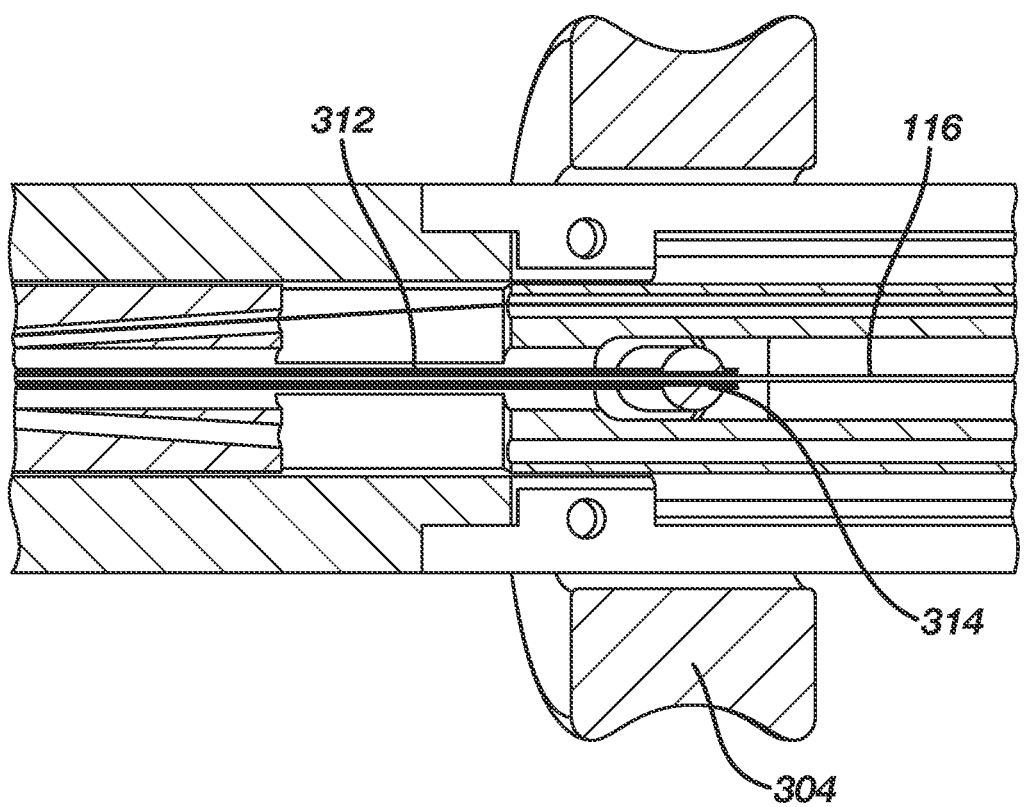
FIG. 11 is the enlarged section A-A of FIG. 10, illustrating the memory shape portion deployment actuator in the undeployed position.
Figure 12:
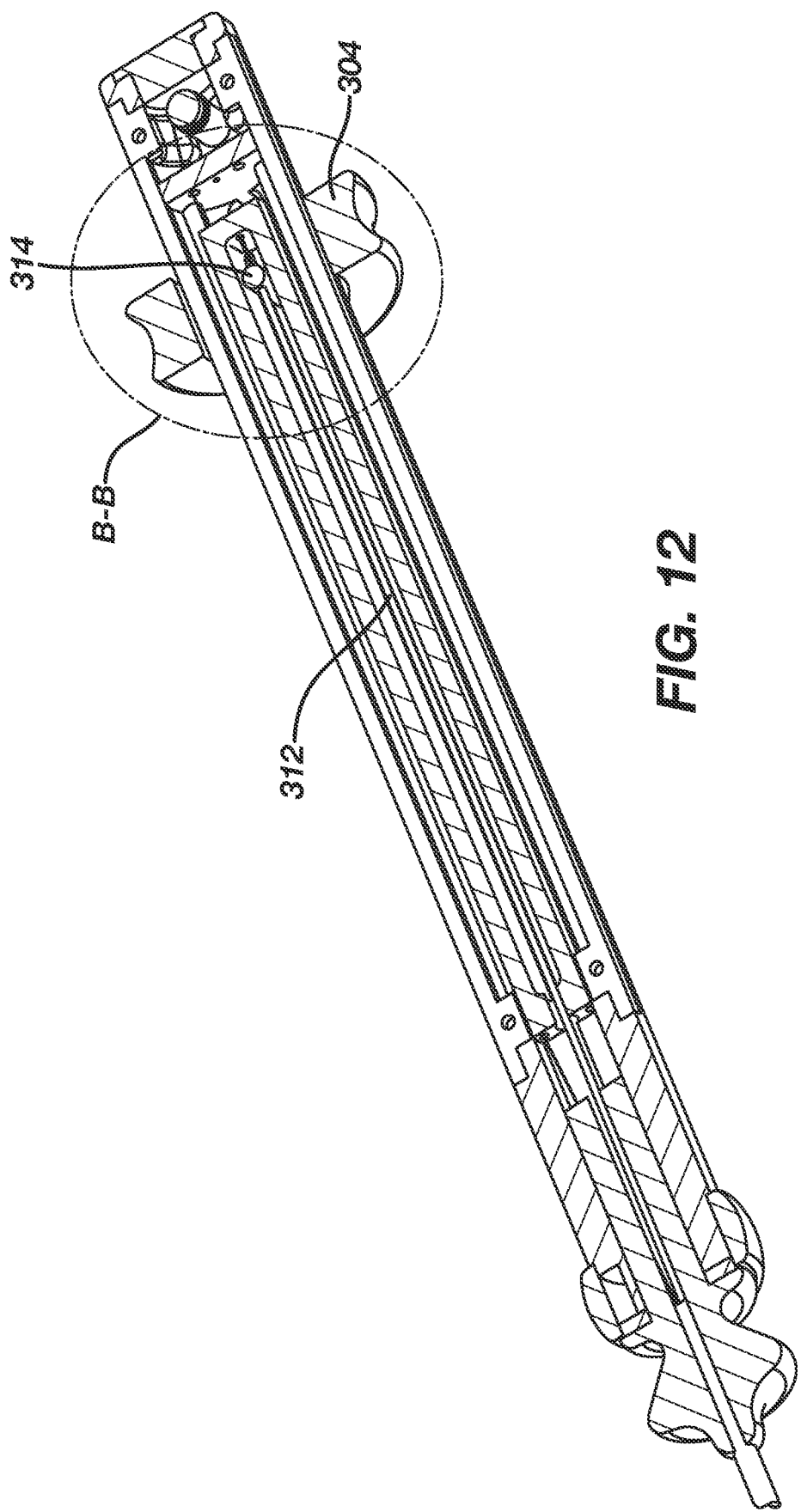
FIG. 12 is a cross-section of an example of a handle of the present disclosure illustrating the elements involved in deploying the helical section in the deployed position.
Figure 13:
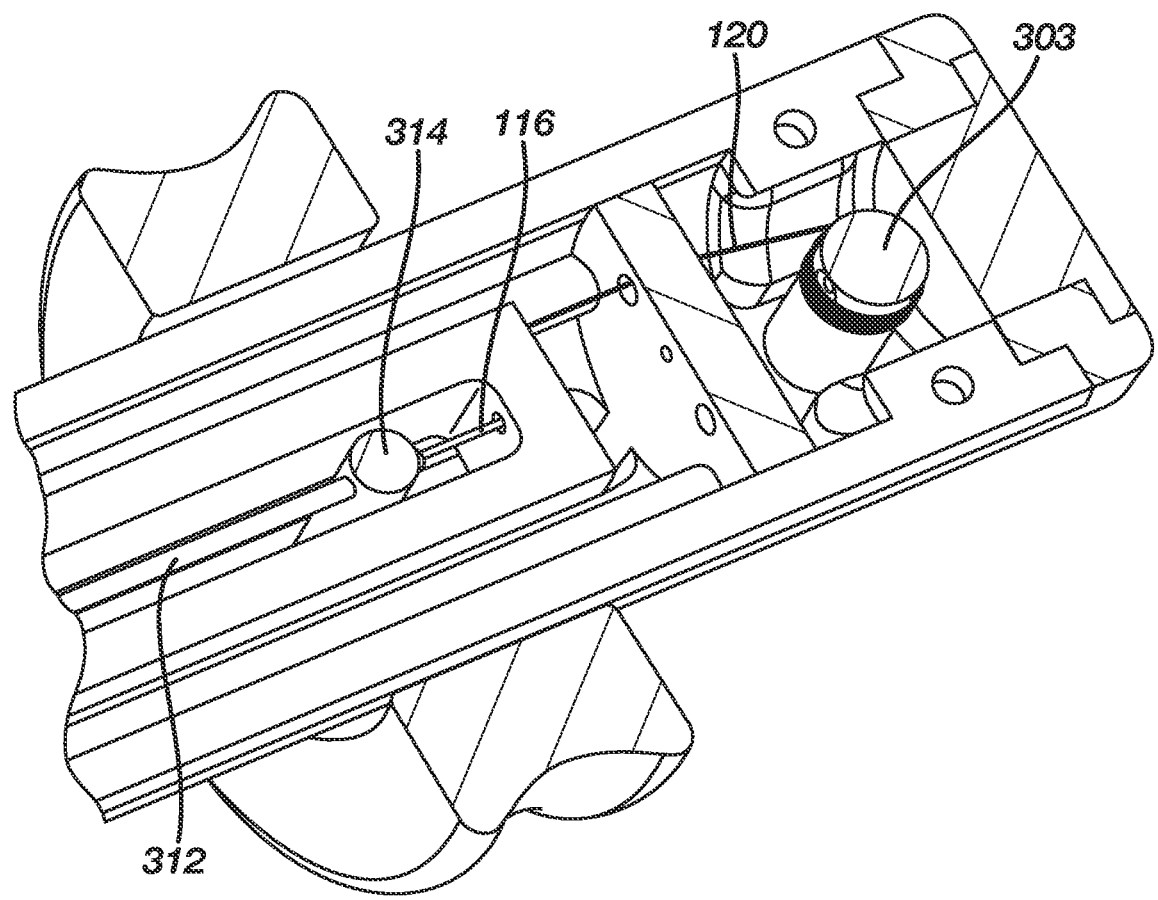
FIG. 13 is the enlarged section B-B of FIG. 12, illustrating the memory shape portion deployment actuator in the deployed position.

FIGS. 10 and 11 illustrate the memory shape portion deployment actuator 304 at the most distal position (its first location) that maintains the cover tube 312 over the shape memory portion 200/shape memory alloy 116 which prevents the shape memory alloy 116 from returning to its predetermined shape. Moving the memory shape portion deployment actuator 304 to a proximal position (its second location) withdraws the cover tube 312 away from the shape memory portion 200/shape memory alloy 116 allowing the shape memory alloy 116 to return to the predetermined shape. This position is illustrated in FIGS. 12 and 13.

Said differently for one example, the cover tube 312 overlays almost the entire catheter 100 from the handle 300 to just before the distal tip 202. The cover tube 312 can be flexible, made from Nitinol, stainless steel, or semi-stiff polymer, the tube can also be laser cut to allow for additional flexibility. The cover tube 312 needs to be stiff enough to constrain the shape memory portion 200/shape memory alloy 116 from returning to its preformed shape, but flexible enough to allow the catheter 100 to traverse the vascular to be deployed in the CS 20. The shape memory alloy 116 is fixed at one end inside the body 301 and the cover tube 312 is deployed over it. The cover tube 312 can be over the outside of the entire catheter 100 or coaxial inside the shape memory lumen 114. The cover tube 312 is shorter in length than the shape memory alloy 116 to the point that when the memory shape portion deployment actuator 304 is distal at the first location, the cover tube 312 covers and constrains the shape memory portion 200. Once the cover tube 312 is pulled back by the memory shape portion deployment actuator 304 being moved to the second location, the difference in length causes the shape memory alloy 116 to now be unconstrained and able to return to its preset shape.

Additionally, either during or after the procedure, the memory shape portion deployment actuator 304 can be moved distal (i.e. back to the first location) to reconstrain the shape memory alloy 116, bringing the catheter 100 back to its delivery configuration to then remove it from the vascular. The shape memory alloy 116 can also be reconstrained if the shape memory portion 200 needs to be repositioned during the procedure for any reason.

Figure 15:
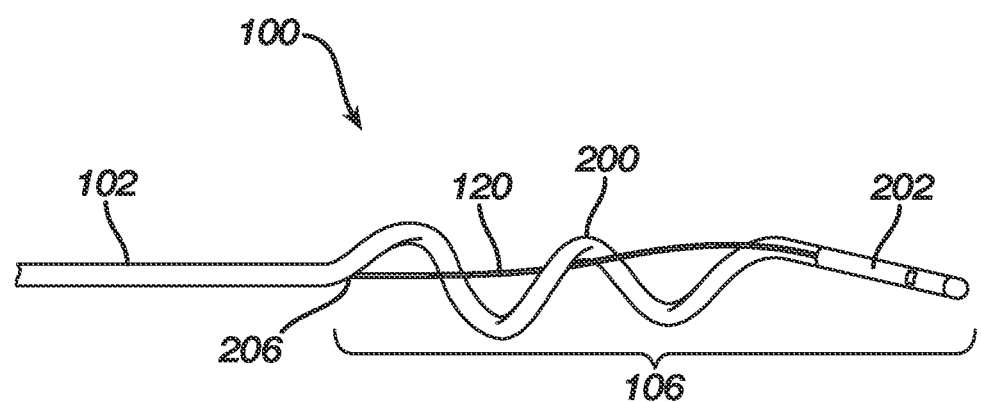
FIG. 15 is a side view of another example of a stabilized coronary sinus catheter of the present disclosure.

FIGS. 15 and 16 illustrate other examples of coronary sinus catheters. FIG. 15 illustrates an example where the pull wire 120 can be used to both deflect the distal tip 202 and then pulled with additional force to deform the shape memory portion 200 into its deployed configuration. In this example, the shape memory alloy 116 can be preset to be straight and the tension pulls the alloy "out of shape" into, for example, a helical shape. In the illustrated example the pull wire 120 in within the pull wire lumen 118 only until the medial section 104. The pull wire 120 is then outside a lumen until the distal tip 202. This allows the distal section 106 to deform under tension.

Figure 16A:
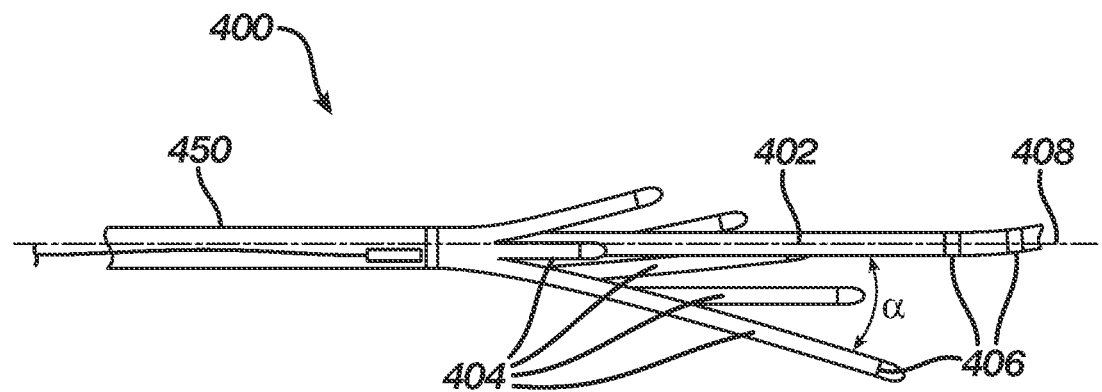
FIGS. 16A and 16B illustrate a side view of a further example of a stabilized coronary sinus catheter of the present disclosure, and it being deployed in the coronary sinus, respectively.
Figure 16B:
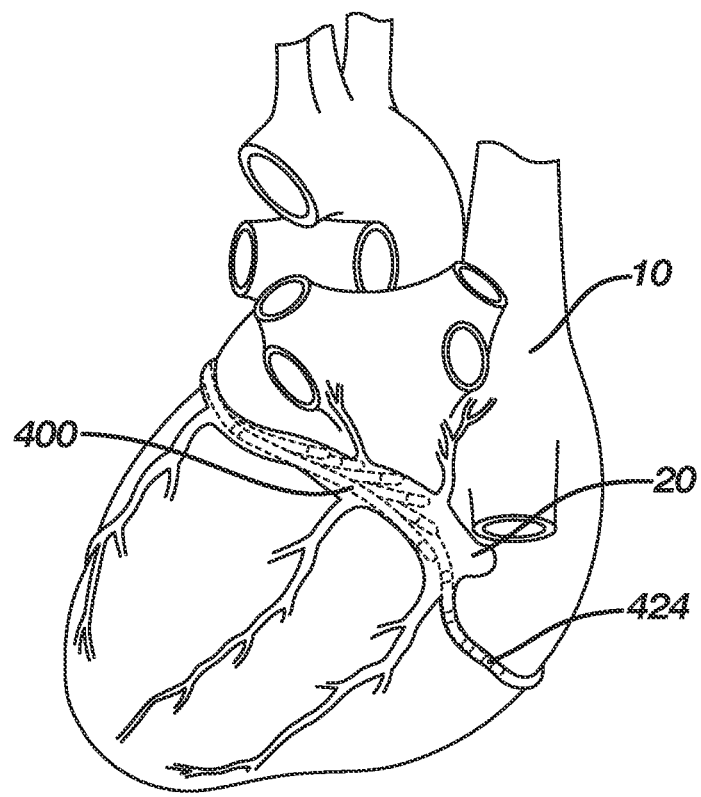

FIGS. 16A and 16B illustrate yet another stabilized coronary sinus catheter 400 having a main sensor probe 402. The main sensor probe 402 can act similar to the distal tip 202 above having at least single axis location sensor 424 to guide the catheter 400 and include a plurality of main sensors 406 disposed along a length of the main sensor probe 402. However, instead of the shape memory portion 200, this example has a plurality of secondary sensor probes 404. The plurality of secondary sensor probes 404 have a second length shorter than the first length and at least one secondary sensor 406 disposed at a distal position/tip. The second (shorter) length can be a plurality of different sub lengths and one or more of the secondary sensor probes 404 can have a different sub length.

A sheath catheter 450 can have a lumen configured to allow the main sensor probe 402 and the plurality of secondary sensor probes 404 to pass therethrough. During delivery, a sheathed position can have the plurality of secondary sensor probes 404 enclosed in the lumen and at least a portion of the main sensor probe 402 outside the lumen. This allows a compact delivery profile to move the catheter 400 through the vascular to the CS 20. Once in the CS 20, the catheter 400 can be unsheathed, and the unsheathed position can have both the main sensor probe 402 and the plurality of secondary sensor probes 404 outside the lumen. Further, the plurality of secondary sensor probes 404 can angle α away from the main sensor probe 402 and apply a lateral force against the coronary sinus 20. This lateral force acts as an anchoring force to stabilize the catheter 400 in the CS 20, for all the reasons noted above.

Descried differently, the catheter 400 can have a midline axis 408 and the main sensor probe 402 is disposed approximately along the midline axis 408. Then, the plurality of secondary sensor probes 404 can be approximately parallel to the midline axis 408 in the sheathed position and form the angle α away from the midline axis in the unsheathed position. Specifically, the secondary sensor probe angle α is formed between at least one of the secondary sensor probes 404 and the midline axis 408. The secondary sensor probe angle α can be between approximately 0° and approximately 90° and more particularly between approximately 0° and approximately 10°. The secondary sensor probes 404 can angle away from the midline axis 408 because they have shape memory alloy or some other form of bias to move them away. The bias can also be formed from thin shaped spring steel or other metals.

Figure 17:
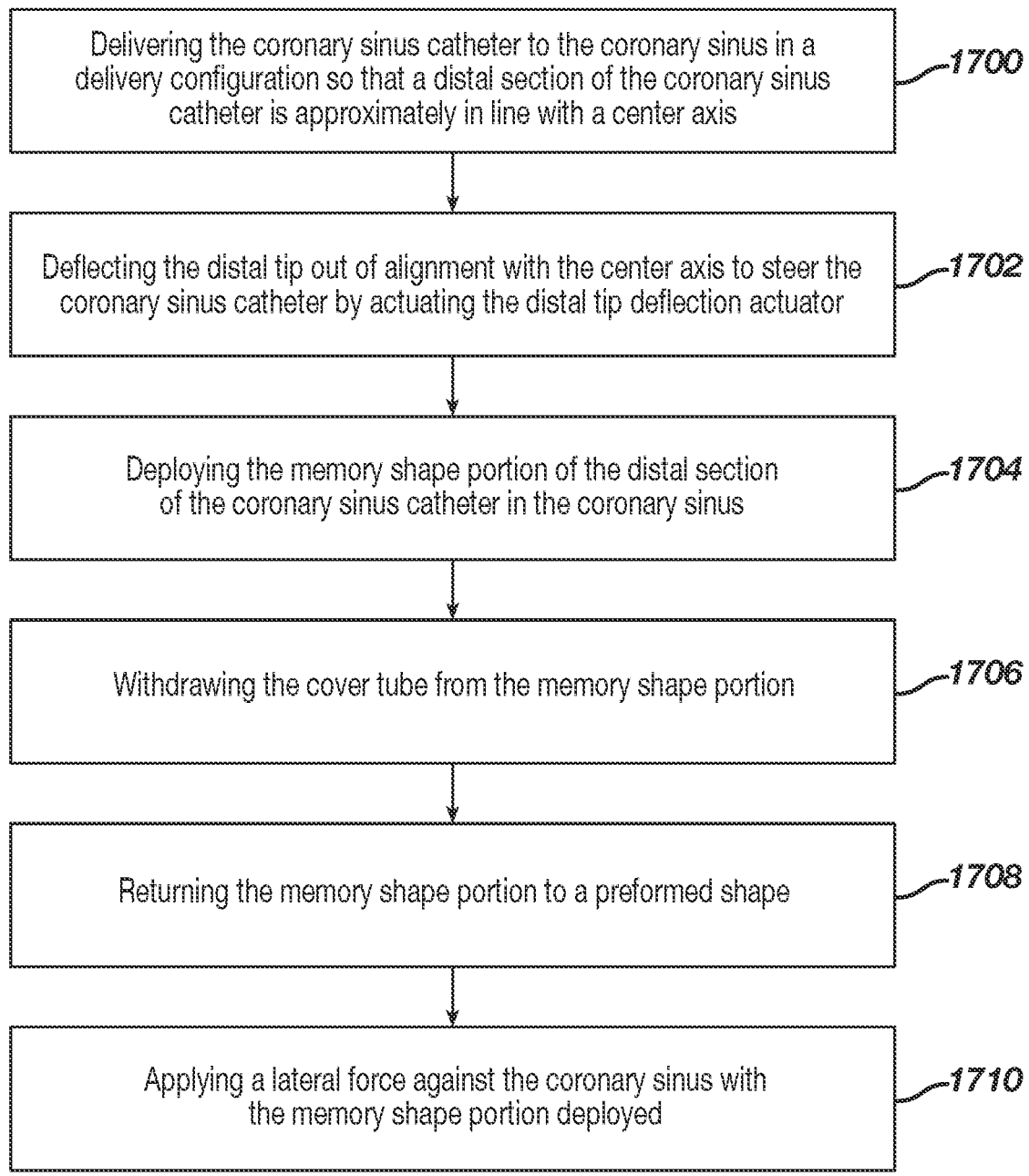
FIG. 17 is a flow diagram illustrating a method of deploying a stabilized coronary sinus catheter with an advanced handle.

FIG. 17 illustrates a method of using a coronary sinus catheter (i.e. 100, 400) to map electrical activity of the heart 10. The coronary sinus catheter 100, 400 can include a distal section 106 with a memory shape portion 200, and a distal tip 202, distal of the memory shape portion 200. Also included is a handle 300, disposed proximal of the proximal section 102 of the catheter with a body 301, a distal tip deflection actuator 302, a memory shape portion deployment actuator 304, a cover tube 312 disposed over a portion of the memory shape portion 200, and a center axis 306. Examples of the steps can include delivering the coronary sinus catheter to the coronary sinus in a delivery configuration so that a distal section of the coronary sinus catheter is approximately in line with a center axis (1700). The distal tip 402 can be deflected out of alignment with the center axis 306 to steer the coronary sinus catheter 100 by actuating the distal tip deflection actuator 302 (1702). The memory shape portion 200 of the distal section 106 can be deployed in the coronary sinus 20 (1704). Deploying the memory shape portion 200 can have the additional steps of withdrawing the cover tube from the memory shape portion (1706) and returning the memory shape portion to a preformed shape (1708). Additionally, the method can include applying a lateral force against the coronary sinus 20 with the deployed memory shape portion 200 (1710).

Certain aspects of the general disclosure can include two configurations, one straight, and another with a helical shape. The helical shape is created with a pre-formed wire of shape memory alloy (nitinol). The configurations are toggled by extending/retracting a tube internal to the catheter shaft. There is a deflectable tip for steerability. Multiple sensors allow visualization in a mapping system. A locking ring is disposed on the plunger/distal tip deflection actuator to prevent unwanted deflection while extending/retracting the tube. A multiple lumen plastic extrusion can be used to keep components separated e.g., electrical wires, nitinol and tube. The electrodes over helical length to allow for multi-circumferential cardiac information.

As to the attachment points within the handle, the puller wire can be anchored distally at distal area of deflectable tip and proximally to a shaft in the proximal area of the handle body. The proximal anchor point of the pull wire allows for adjustment of tension in the wire during assembly. The nitinol wire with a pre-formed helix shape can be anchored distally to the catheter tip, distal of the helix shape. The nitinol wire can be further anchored proximally at the proximal end of the plunger part. This allows the entire length of nitinol wire to move together with the shaft during tip deflection. The tube's distal end floats free in the catheter lumen and is anchored to a stud located in the handle.

The nitinol and tube also have an exemplary behavior where the nitinol wire acts as a guide and bearing surface for the tube which passes over it. The tube has two sections, a distal section is more flexible to facilitate motion over the helical shape, and through the anatomy. The proximal section is stiffer to allow higher force transmission. To reduce friction during tube extension/retraction, a lubricant is used on the interfaces of nitinol wire and tube. The lubricant can also be used between the tube and catheter lumen. The tube assembly can have protrusions with smooth contours ("beads") around the outer circumference, spaced along the distal length, including at the distal tip, to reduce friction during tube extension/retraction. The plunger and handle have clearance for the tube anchoring stud to allow for movement of the tube relative to these components.

Examples regarding the tip deflection which include that the handle has a stroke limiting feature that allows adjustment of allowable pull wire deflection during assembly. Wire coils can be used in the shaft section immediately proximal and distal of the helical area, but not in the helical area, to add stiffness to the catheter which improves tip deflection. However, the distal deflectable tip is soft yet allows for deflection.

Other features of a stabilized coronary sinus catheter with distal strain relief have a proximal section including a proximal stiffness, a medial section, distal of the proximal section, including a medial stiffness, and a distal section, distal of the medial section. The distal section can include a memory shape portion, a distal tip, distal of the memory shape portion, a shape memory lumen disposed along the shape memory portion, and a shape memory alloy, disposed in the shape memory lumen. There can be a delivery configuration including the memory shape portion and the distal tip approximately in line with a center axis and a deployed configuration including the memory shape portion forming a shape approximately conforming to the shape of the coronary sinus. The distal tip can include a flexibility greater than the proximal stiffness, the medial stiffness, and a stiffness of the shape memory alloy.

The stabilized coronary sinus catheter can have the distal tip configured to hang in the right atria when in the deployed configuration. The shape of the shape memory portion can have an approximately helix shape and configured to apply a lateral force to the coronary sinus. Also, the helix can be formed along a distal section axis offset from the center axis. A plurality of sensors can be disposed along the distal section and a sensor wire lumen, including a sensor cable disposed therein, can connect the plurality of sensors.

A guidewire lumen can be further disposed from the proximal section to the distal section so that the delivery configuration further has the distal section conforming to a shape of a guidewire disposed in the guidewire lumen. Then the deployed configuration occurs when the guidewire is partially removed from the guidewire lumen. A pull wire lumen can additionally be disposed from the proximal section to the distal tip and a pull wire disposed in the pull wire lumen. A neutral position can include the distal tip approximately in line with the center axis and a deflected position displacing the pull wire with the distal tip moving out of alignment with the center axis.

Another stabilized coronary sinus catheter system can have the coronary sinus catheter with a proximal section, a distal section (including a memory shape portion, and a distal tip, distal of the memory shape portion), a shape memory lumen disposed along the shape memory portion, and a shape memory alloy disposed in the shape memory lumen. The handle can be disposed proximal of the proximal section and include a distal tip deflection actuator, a memory shape portion deployment actuator; and a center axis. A neutral position can include the distal tip approximately in line with the center axis and the distal tip deflection actuator at a first position and the deflected position including the distal tip moving out of alignment with the center axis and the distal tip deflection actuator at a second position. Next a delivery configuration can include the memory shape portion and the distal tip approximately in line with a center axis and the memory shape portion deployment actuator at a third position, and a deployed configuration including the memory shape portion forming a shape approximately conforming to the shape of the coronary sinus and the memory shape portion deployment actuator at a fourth position.

The pull wire lumen can be disposed from the proximal section to the distal tip with a pull wire disposed in the pull wire lumen. The distal tip deflection actuator can be attached to the pull wire, and the second position displaces the pull wire. The guidewire lumen is disposed from the proximal section to the distal section.

A medial section, distal of the proximal section, can include a medial stiffness, the proximal section comprises a proximal stiffness, and the distal tip include a flexibility greater than the proximal stiffness, the medial stiffness, and a stiffness of the shape memory alloy. A plurality of sensors can be disposed along the distal section, and a sensor wire lumen has a sensor cable disposed therein connecting the plurality of sensors.

A method of using a coronary sinus catheter to map electrical activity of a heart, includes the steps of delivering the coronary sinus catheter to the coronary sinus in a delivery configuration so that a distal section of the coronary sinus catheter is approximately in line with a center axis. Deploying a memory shape portion of the distal section of the coronary sinus catheter in the coronary sinus and dangling a distal tip of the distal section in the right atria when the memory shape portion is deployed. The method further includes applying a lateral force against the coronary sinus when the memory shape portion is deployed.

A further stabilized coronary sinus catheter includes a main sensor probe including a plurality of main sensors disposed along a first length of the main sensor probe and a plurality of secondary sensor probes. The secondary sensor probes each including a second length shorter than the first length, and a secondary sensor disposed on the distal position. A sheath catheter can have a lumen configured to allow the main sensor probe and the plurality of secondary sensor probes to pass therethrough. A sheathed position can have the plurality of secondary sensor probes enclosed in the lumen and at least a portion of the main sensor probe is outside the lumen. The unsheathed position includes both the main sensor probe and the plurality of secondary sensor probes are outside the lumen, and the plurality of secondary sensor probes angled away from the main sensor probe and applying a lateral force against the coronary sinus.

The stabilized coronary sinus catheter second length has a plurality of sub lengths, and a portion of the plurality of secondary sensor probes each have a different sub length. A midline axis is included, and the main sensor probe is disposed approximately along the midline axis. Also, the plurality of secondary sensor probes are approximately parallel to the midline axis in the sheathed position and form an angle away from the midline axis in the unsheathed position. A secondary sensor probe angle can be formed between a secondary sensor probe and the midline axis. Here, the secondary sensor probe angle can be between approximately 0° and approximately 90°. More specifically, the secondary sensor probe angle can be between approximately 0° and approximately 10°.

The descriptions contained herein are examples of embodiments of the disclosure and are not intended in any way to limit the scope of the disclosure. As described herein, the disclosure contemplates many variations and modifications of ablation tools and diagnostic tools, including alternative numbers of electrodes, alternative combinations of electrodes, combinations of components illustrated in separate figures, alternative materials, alternative component geometries, and alternative component placement. Modifications and variations apparent to those having ordinary skill in the art according to the teachings of this disclosure are intended to be within the scope of the claims which follow.

What is claimed is:

1. A stabilized coronary sinus catheter system comprising:
    a coronary sinus catheter comprising:
        a proximal section comprising a proximal stiffness;
        a medial section, distal of the proximal section and comprising a medial stiffness; and
        a distal section comprising:
            a memory shape portion;
            a distal tip, distal of the memory shape portion; and
            a flexibility greater than the proximal stiffness, the medial stiffness, and a stiffness of the memory shape portion;
    a handle, disposed proximal of the proximal section comprising:
        a body defining a center axis;
        a distal tip deflection actuator configured to be in one of a first, second, or third position along the center axis so that:
            (a) in the first position of the actuator, the distal tip is approximately in line with the center axis;
            (b) in the second position of the actuator for deflection of the distal tip, the distal tip is out of alignment with the center axis; and
            (c) in the third position of the actuator for delivery, the memory shape portion and the distal tip being approximately in line with the center axis; and
        a memory shape portion deployment actuator configured to be in one of a first and second locations with respect to the center axis so that the memory shape portion deployment actuator is in the first location during delivery or deflection of the tip and in the second location for deployment of the memory shape portion that forms a predetermined shape approximately conforming to the shape of a coronary sinus of a patient.

2. The stabilized coronary sinus catheter system of claim 1, further comprising:
    a pull wire, comprising:
        a first end anchored in the distal tip; and
        a second end fixed in the body;
    the distal tip deflection actuator attached to the pull wire and configured to displace the pull wire when in the second position.

3. The stabilized coronary sinus catheter system of claim 1, wherein the actuator deflecting the distal tip causes the distal tip to deflect over a deflection angle between approximately 0° and approximately 180° with respect to the center axis.

4. The stabilized coronary sinus catheter system of claim 1, further comprising:
    a single axis location sensor disposed approximately at the distal tip.

5. The stabilized coronary sinus catheter system of claim 1, further comprising:
    a deflection actuator lock comprising:
        an unlocked position permitting the distal tip deflection actuator to move between the first position and the second position; and
        a locked position preventing the distal tip deflection actuator to move between the first position and the second position.

6. The stabilized coronary sinus catheter system of claim 1, further comprising:
    a shape memory alloy disposed along the shape memory portion and comprising one end fixed in the body;
    a cover tube disposed over a portion of the shape memory alloy and comprising a memory shape portion deployment end fixed to the memory shape portion deployment actuator;
    in a delivery configuration the cover tube constrains the shape memory alloy; and
    in a deployed configuration the shape memory alloy is unconstrained by the cover tube.

7. The stabilized coronary sinus catheter system of claim 6,
    the memory shape portion deployment actuator at the first location maintains the cover tube over the shape memory alloy preventing the shape memory alloy from returning to the predetermined shape; and
    the memory shape portion deployment actuator at the second location withdraws the cover tube away from the shape memory alloy allowing the shape memory alloy to return to the predetermined shape.

8. The stabilized coronary sinus catheter system of claim 1, the predetermined shape of the shape memory portion comprises approximately a helical shape.

9. The stabilized coronary sinus catheter system of claim 8, the predetermined shape of the shape memory portion comprises at least one of:
   a proximal section bending radius between approximately 8.5 mm and approximately 9.5 mm;
   a distal section bending radius between approximately 7.0 mm and approximately 8.0 mm;
   a proximal section helix angle between approximately 110° and approximately 120°;
   a distal section helix angle between approximately 150° and approximately 160°;
   a shape memory portion length between approximately 42.5 mm and approximately 44.5 mm;
   a major diameter of a first helix coil approximately 14.0 mm and approximately 16.0 mm; and
   a taper angle between approximately 3.5° and approximately 5.5°.

10. A method of using a coronary sinus catheter to map electrical activity of a heart, the coronary sinus catheter comprising a distal section comprising a memory shape portion, and a distal tip, distal of the memory shape portion; a handle, disposed proximal of a proximal section comprising: a body; a distal tip deflection actuator; a memory shape portion deployment actuator; a cover tube disposed over a portion of the memory shape portion, and a center axis; wherein the distal section comprises a flexibility greater than a proximal stiffness, a medial stiffness, and a stiffness of the memory shape portion; the method comprising the steps of:
   delivering, to a coronary sinus of a patient, the coronary sinus catheter in a delivery configuration so that the distal section of the coronary sinus catheter is approximately in line with the center axis;
   deflecting the distal tip out of alignment with the center axis to steer the coronary sinus catheter by actuating the distal tip deflection actuator; and
   deploying the memory shape portion of the distal section of the coronary sinus catheter in the coronary sinus to prevent movement of the memory shape portion, comprising the steps of:
      withdrawing the cover tube from the memory shape portion; and
      returning the memory shape portion to a preformed shape.

11. The method of claim 10, further comprising:
   applying a lateral force against the coronary sinus with the memory shape portion deployed.

* * * * *